United States Patent
Araki et al.

[11] Patent Number: 6,135,710
[45] Date of Patent: Oct. 24, 2000

[54] TURBO BLOOD PUMP

[75] Inventors: Kenji Araki, Miyazaki; Hirohumi Anai, Ooita, both of Japan

[73] Assignee: JMS Co., Ltd., Hiroshima, Japan

[21] Appl. No.: 08/942,680

[22] Filed: Oct. 2, 1997

[30] Foreign Application Priority Data

Oct. 2, 1996 [JP] Japan ..................................... 8-281460

[51] Int. Cl.[7] .............................. F04D 7/02; F04D 29/24; A61M 1/12

[52] U.S. Cl. .......................... 415/206; 415/229; 415/900; 416/179; 416/182; 416/183; 416/223 R; 416/223 B; 417/420; 417/423.12; 600/16; 623/3

[58] Field of Search ..................... 415/206, 229, 415/900; 416/179, 183, 185, 186 R, 188, 182, 223 R, 223 B; 417/420, 423.12, 423.13; 600/16, 17; 623/3

[56] References Cited

U.S. PATENT DOCUMENTS

| | | |
|---|---|---|
| 3,644,056 | 2/1972 | Wiselius .................................. 416/188 |
| 4,507,048 | 3/1985 | Belenger et al. ........................ 415/900 |
| 5,324,177 | 6/1994 | Golding et al. . |
| 5,370,509 | 12/1994 | Golding et al. . |
| 5,601,418 | 2/1997 | O'Hara et al. .......................... 417/420 |

FOREIGN PATENT DOCUMENTS

| | | | |
|---|---|---|---|
| 583781 | 2/1994 | European Pat. Off. .......... | 417/423.12 |
| 913527 | 9/1946 | France .................................... | 415/206 |
| 2-99800 | 4/1990 | Japan . | |
| 5-312185 | 11/1993 | Japan .................................... | 416/185 |
| 6-218043 | 8/1994 | Japan . | |
| 7-178165 | 7/1995 | Japan . | |
| 144659 | 4/1931 | Switzerland ....................... | 416/186 R |
| 979432 | 1/1965 | United Kingdom .................. | 416/183 |

*Primary Examiner*—Christopher Verdier
*Attorney, Agent, or Firm*—Cummings & Lockwood

[57] ABSTRACT

A blood pump used for extra corporeal circulation, and more particularly, as a small turbo blood pump including a casing having an interior region, an aperture formed in an upper portion defining a blood inlet, and an aperture formed in a lower portion defining a blood outlet. An impeller is rotatably mounted within said casing interior region and includes a rotary shaft and at least one vane depending therefrom. The at least one vane has an upper radius adjacent the blood inlet that is less than a lower radius adjacent the blood outlet. The base of the at least one vane forms an exterior angle of less than 90° with the axis of the rotary shaft. A driven magnet is mounted to the at least one vane. The impeller is rotationally driven by a non-contacting driving magnet that is exterior to the casing.

36 Claims, 2 Drawing Sheets

TURBO BLOOD PUMP

BACKGROUND OF THE INVENTION

1. Field of the Invention

This invention relates to a turbo blood pump that is extra corporeal or At implantable in a patient's body so as to conduct circulatory assistance or extra corporeal circulation of blood for a cardiopulmonary bypass operation, hemo purification, or other treatments.

2. Description of the Related Art

Conventionally, a roller blood pump for pumping out blood by compressing a tube was often used for extra corporeal circulation. However, this kind of roller pump needs a special pump segment tube to be fit thereto, and the lack of strength and durability of the tube causes problems. A further important problem is that the roller type blood pump is bulky and difficult to handle. Thus it is difficult to use, for example, in the sterile area of an operating field. Therefore, in recent years, turbo blood pumps such as centrifugal pumps and axial flow pumps, which can be used, for example, in the sterile area of an operating field, have been developed. See, for example, Japanese Granted Patent No. 1914715, Japanese Unexamined Patent Publication No. 4-2358, Japanese Unexamined Patent Publication No. 6-218043, Japanese Granted Utility Model No. 1792315, Japanese Unexamined Patent Publication No. 2-99800, Japanese Unexamined Patent Publication No. 7-75667, and Japanese Unexamined Patent Publication No. 7-178165.

In the centrifugal pump, liquid is fed into a casing inlet and flows substantially perpendicular to an impeller axis. In comparison, in an axial flow pump liquid is fed into a casing and flows in parallel to the axis. When developing these pumps, it is necessary to design the suitable rotation number in order to feed liquid efficiently or feed liquid so as to assure a stable state in which, for example, flow separation, collision, vortex, cavitation or the like is not caused. That is, a relatively low rotation number in a range of 1,000–4,000 rpm is desired to feed liquid efficiently by means of a normal left ventricular assistance centrifugal type pump (flow rate: 5L/min, pressure head: 100 mm Hg). Further, a relatively high rotation number in a range of 9,000–30,000 rpm is desired to feed liquid efficiently by means of an axial flow pump.

The discharge rate (flow rate) of the above turbo type pumps is determined mainly by the rotation speed and the size of the impeller. Thus, to assure a large discharge rate in a centrifugal type pump, the size of the pump including the impeller and casing needs to be enlarged. Generally, a centrifugal pump used for extra corporeal circulation has an impeller diameter as large as 40–80 mm and a large priming volume. However, as will be described later, enlargement of the pump is not desirable.

On the other hand, because the axial flow pump ensures a larger rotation number to achieve efficient fluid feeding than the centrifugal pump, it can provide a large discharge rate if the same impeller diameter is used. However, conventional axial flow pumps could not provide a sufficient driving power for cardiopulmonary bypass, because they were about 5–16 mm in impeller diameter. Furthermore, the axial flow pump has a higher impeller rotation number than the centrifugal pump, and, therefore, blood injury such as hemolysis is more likely to occur. Thus, usually, the axial flow pump is designed so that the rotation speed is low and the impeller vane is as large as possible, in order to reduce a possibility of hemolysis. However, in this case, hydraulic efficiency drops so that the advantage of the axial flow pump is not fully realized.

Further, because the conventional turbo blood pump of, for example, a centrifugal pump, is connected to a driving source, many types have shaft sealing. However, a blood pump having shaft sealing is difficult to operate for more than two weeks because a lack of durability of th-e shaft sealing. Also, because thrombus is likely to occur, shaft sealing is a problem with respect to anti-thrombogenicity. To solve the above problem, an impeller that does not require shaft seals was developed. Such an impeller is disclosed in U.S. Pat. No. 4,507,048 issued to Belenger et al. According to this invention, the upper and lower ends of the rotary shaft of the impeller are supported in the casing. External to the casing is a magnetic driving mechanism such as an electric coil which generates a rotating magnetic field for driving the impeller. A disadvantage of this invention is that rotor stability is lost when the supporting means is deformed. Deformation is caused by variations in the distance between the upper and lower bearings and the contacting pressure of the upper and lower supporting structure. Such deformation may cause hemolysis and thrombus formation in the blood pump.

SUMMARY OF THE INVENTION

Accordingly, an object of the present invention is to provide a blood pump which can be installed in, for example, the sterile area of an operating field, and will not disturb the operation procedure. Another object of the present invention is to provide a small-size, implantable blood pump which can be implanted in the body and will reduce anatomical limitations at the time of implantation, thereby simplifying operation. Yet another object of the present invention is to provide a blood pump which has a sufficient discharge rate and driving power—thereby achieving efficient feeding of liquid. A further object of the present invention is to provide a blood pump which reduces an influence upon blood due to dynamic action such as shear stress and heat generation, thereby reducing damage upon blood such as hemolysis. A still further object of the present invention is to provide a blood pump which limits the formation of thrombus and is highly durable.

According to a first aspect of the present invention, there is provided a turbo blood pump including an impeller having a rotary shaft and vanes formed so as to connect to the rotary shaft. The impeller is mounted to rotate within a casing and about the rotary shaft. The top of the casing includes a blood inlet while the bottom of the casing includes a blood outlet. The vanes taper out radially from the inlet to the outlet. The casing closely follows the impeller taper. Means is provided for rotating the impeller. The bottom edge of the impeller as viewed from the side forms an angle ($\delta$) between $0°<\delta<65°$ with the axis of the rotary shaft.

According to a second aspect of the present invention, there is provided a turbo blood pump according to the first aspect wherein, at least, a part of the impeller vane is a three-dimensional structure vane which is not in parallel relation to the rotary axis of the impeller (hereinafter referred to as the vane structure 1).

According to a third aspect of the present invention, there is provided a turbo blood pump according to the first aspect wherein the impeller vane is of a three-dimensional structure formed of twisted curved faces (hereinafter referred to as the vane structure 2).

According to a fourth aspect of the present invention, there is provided a turbo blood pump according to the first aspect wherein an angle formed by the impeller vane relative to a circumference at an upper end of the vane at the exit is different from an angle formed thereby relative to a circumference at a bottom end of the vane at the exit (hereinafter referred to as the vane structure 3).

According to a fifth aspect of the present invention, there is provided a turbo blood pump according to the first aspect wherein an upper portion and lower portion of the impeller rotary shaft are structured in a pivot bearing structure and sliding bearing structure, the sliding bearing of the cylindrical face contacting type. A driven magnet is mounted on the impeller, so that the driven magnet is magnetically coupled with a driving magnet mounted outside the casing, the driving magnet radially adjacent to the impeller rotary shaft. (hereinafter referred to as the shaft structure 1).

Further, by combining the above vane structures 1–3 and the shaft structure 1, a more preferable turbo blood pump can be realized.

According to a sixth aspect of the present invention, there is provided a turbo blood pump mentioned above, further comprising an impeller having a vane structure in which the vane structure 1 and the vane structure 3 are combined (hereinafter referred to as the vane structure 4).

According to a seventh aspect of the present invention, there is provided a turbo blood pump mentioned above, further comprising an impeller having a vane structure in which the vane structure 2 and the vane structure 3 are combined (hereinafter referred to as the vane structure 5).

According to an eighth aspect of the present invention, there is provided a turbo blood pump mentioned above in which the vane structure 1 and the shaft structure 1 are combined.

According to a ninth aspect of the present invention, there is provided a turbo blood pump mentioned above in which the vane structure 2 and the shaft structure 1 are combined.

According To a tenth aspect of the present invention, there is provided a turbo blood pump mentioned above in which the vane structure 3 and the shaft structure 1 are combined.

According to an eleventh aspect of the present invention, there is provided a turbo blood pump mentioned above in which the vane structure 4 and the shaft structure 1 are combined.

According to a twelfth aspect of the present invention, there is provided a turbo blood pump in which the vane structure 5 and the shaft structure 1 are combined.

The above and other features of the subject invention will be made more readily apparent to those having ordinary skill in the art from the following detailed description of the invention taken in conjunction with the accompanying drawings.

BRIEF DESCRIPTION OF THE DRAWINGS

Although the turbo blood pump of the present invention can be embodied in various ways in terms of its components and allocation, preferred drawings and embodiments are described and illustrated below.

DETAILED DESCRIPTION OF THE PREFERRED EMBODIMENTS

Features and preferred embodiments of a turbo blood pump of the present invention will be described in detail with reference to the accompanying drawings.

1. Pump Flow Type

Turbo pumps may be generally classified as centrifugal flow pumps, mixed flow pumps, or axial flow pumps. The turbo blood pump of the present invention will be described in detail with respect to each component.

Figure 1:
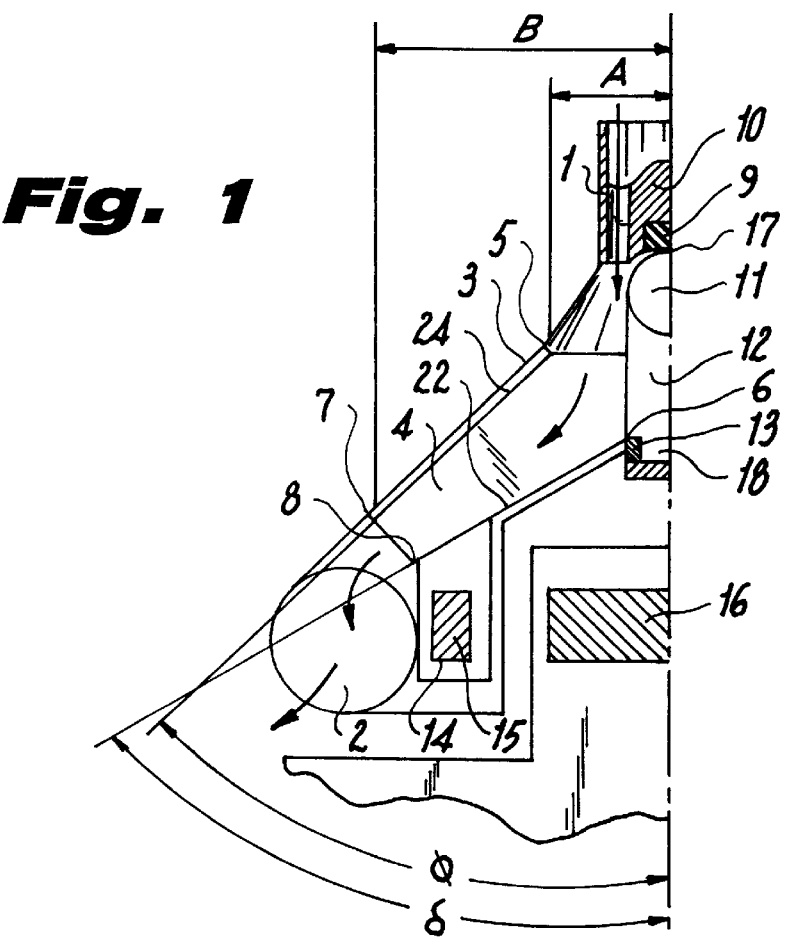
FIG. 1 is a side elevational view in cross-section of a turbo blood pump according to the present invention with magnetic coupling in the radial direction.

With respect to its small size and discharge rate, the mixed flow pump is most desirable. Referring to FIG. 1, there is illustrated a mixed flow pump of the present invention. In the mixed flow pump, blood in an impeller flows neither parallel or perpendicular to the pump axis, but in an oblique direction as illustrated by the arrows. The mixed flow pump utilizes a centrifugal force so as to give energy to fluid such as blood. Thus, the impeller of the mixed flow pump has a larger diameter at its vane exit (2×B) than at its vane entrance (2×A)—unlike the axial flow pump. The bottom of the vane 22 has an exterior angle $\delta$ of $0°<\delta<90°$ with the axis of the impeller shaft. In viewpoints of efficiency of flow and damage upon fluid, the above angle $\delta$ is preferred to be $0°<\delta<65°$, and $25°<\delta<65$ is further preferable. The optimum specific speed of the mixed flow type blood pump is higher than the centrifugal pump, thus a higher rotation number and thereby a higher efficiency can be obtained. Because the higher rotation number is achieved, the size of the impeller and casing can be reduced, so that reduction of the pump size and assurance of the large discharge rate are achieved without decreasing the efficiency.

2. Impeller Structure a. Three-dimensional Structure of the Vanes

Because, in the turbo blood pump according to the present invention, the upper portion and lower portion of the impeller vane have different diameters at both the entrance and exit ((2×A) and (2×B)), respectively, as a result of considering optimization of blood flow in the pump, it has been found that the vane shape is desired to be of the above vane structures 1–5. The vane structures 4, 5 are further preferable. The above vane structures are favorable in either the mixed flow pump or the non-mixed flow pump, and particularly it has been recognized that they are further favorable in the mixed flow pump. In the case of the vane structure 3, as shown in the plan view of FIG. 5, the upper end of the vane 7 reaches a more outside circumference (virtual circumference D) than the circumference (virtual circumference C) of bottom end thereof.

Figure 5:
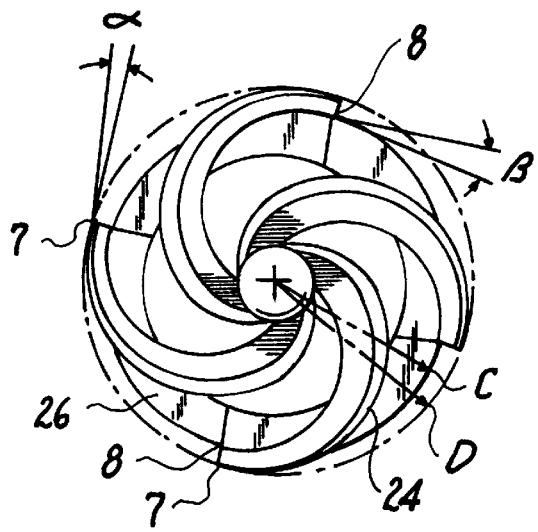
FIG. 5 is a top plan view of the impeller of FIG. 2 as viewed along line 5—5 including four vanes and a vane-attaching disk 26, and illustrating the relationship between the vane top face angle ($\alpha$) and the vane base angle ($\beta$).

With continuing reference to FIG. 5 there is illustrated the vane top face angle a and the vane base angle $\beta$. The top face angle $\alpha$ is defined as the angle formed between a line tangent to the top face of said vane at a point 7 on virtual circumference D and a line tangent the circle formed by the impeller vane at that point 7. The vane base angle $\beta$ is defined as the angle formed between a line tangent the base of said vane at a point 8 on virtual circumference C and a line tangent the circle formed by the impeller vane at that point 8.

The turbo blood pump of the present invention has a three-dimensional structure in that the impeller vane is twisted with respect to the rotational axis as described above. Thus, blood flow disturbances such as flow separation, collision, vortex formation, cavitation or the like are reduced. That is the blood flow is made more efficient. Further, if the blood flow is made efficient, shear stress of blood is reduced, so that generation of heat due to energy loss in the pump is suppressed. As a result, hemolysis is suppressed, the durability of the impeller vane and rotary shaft subjected to high speed rotation is improved, formation of thrombus is suppressed and other effects are produced.

b. Vane Diameter

Referring to FIG. 1, the diameter of the vane (2×B) of the turbo blood pump of the present invention is preferred to be in a range of 4–80 mm. A range of 15–40 mm is further preferred. Such a blood pump in which the impeller vane diameter is 15–30 mm is most suitable for use in a long-term implantation type artificial heart. Further, a blood pump having a diameter of 20–40 mm is suitable for extra corporeal circulation or paracorporeal circulatory assistance because it can generate a higher pressure head than the former.

c. Vane Material and Thickness

The material forming the vanes is required to have the following characteristics; (1) harmless to the human body (excellent bio-compatibility), (2) excellent long-term durability, (3) ability of being precision processed, (4) excellent in hemo-compatibility such as anti-thrombogenicity, (5) appropriate hardness, etc. For example, synthetic resin such as acrylic, polyacrilate, polymetacrilate, polycarbonate and fluoresin and stainless steel, titanium, titanium alloy, fine ceramics or the like are preferable materials.

If the thickness of the vane is too small, there is a problem in strength and durability. If the thickness thereof is too large, too much driving energy is loaded thereon. The preferred thickness of the vane is 1.5–2.0 mm when using polyacrilate and polymetacrilate, 1.0–1.5 mm when using polycarbonate (which has a higher strength than the former), and 0.5–1.5 mm when using stainless, titanium, titanium alloy or the like.

If the thickness of the vane is made to vary gradually from the proximal end of the vane to the distal end thereof, it is effective for maintaining a flow path in the pump or ensuring efficient flow. By gradually thinning the vane from the proximal end to the distal end, flow separation can be reduced so that turbulent flow near the exit is reduced. By gradually thickening the vane structure, the percentage of blood flow at the entrance can be increased.

d. Number of Vanes

Usually there are provided 2–8 vanes, however 3 vanes are preferred. A blood pump having an impeller comprising one vane cannot produce a stable driving force and a blood pump having nine or more vanes is difficult to produce.

e. Other Impeller Structure

In the turbo blood pump of the present invention, a full-open impeller is employed. A full-open impeller is one in which there are no attaching discs attached to, and connecting, either the upper or lower portions of the vanes. As a result, a structure without blood stagnation is provided, so that a place likely to form thrombus is eliminated, thereby achieving excellent anti-thrombogenicity.

An alternate embodiment impeller includes one or more vane-attaching disks. Such an embodiment may include one or more disks extending either partially or fully, or a combination thereof, along the upper and/or the lower portion of each vane. A fully enclosed impeller includes an impeller blood inlet and impeller blood outlet allowing the blood to pass across the vane faces and between the vane-attaching disks.

3. Impeller Shaft and Bearing Structures, and Magnet Coupling System for Driving the Impeller a. Material Forming the Shaft The impeller shaft is to be formed of material having the following characteristics; (1) excellent in hemo-compatibility such as anti-thrombogenicity, (2) suitable hardness, for example, stainless steel, titanium, ceramics or the like is preferable. A bearing for supporting such a shaft is desired to be formed of material having excellent anti-abrasion in addition to the above characteristics. For example, highly durable plastic such as ultra-high density polyethylene or ultra-high molecular weight polyolefin (e.g., Lubmer™ manufactured by MITUI SEKIU KAGAKU Co. Ltd.)

b. Bearing Structure and Magnet Coupling System

Figure 3:
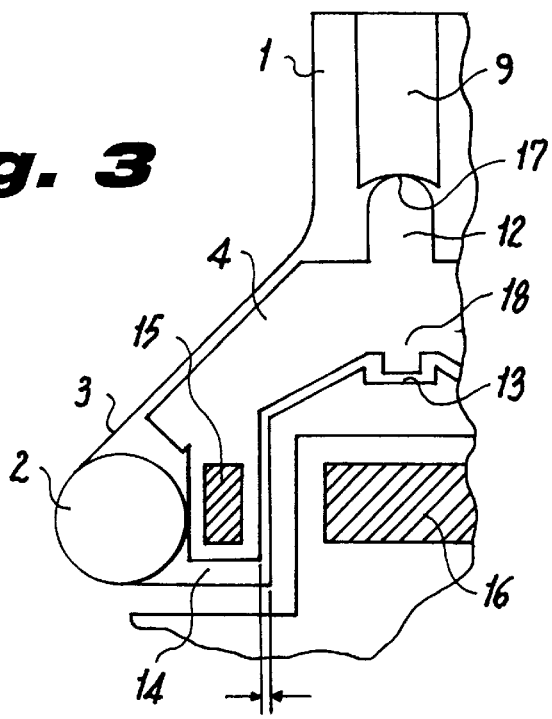
FIG. 3 is a side elevational view in cross-section of another turbo blood pump constructed in accordance with a preferred embodiment of the subject invention with magnetic coupling in the radial direction.

As shown in FIG. 3, a magnet casing 14 is mounted to the impeller vane 4 and a driven magnet 15 is mounted within the magnet casing 14. The driven magnet 15 is magnetically coupled with a driving magnet 16 mounted outside the magnet casing 14 and radially adjacent the driven magnet 15. As a result, a force of the magnetic coupling is not applied to shaft 12 and pivotal bearing 9 and sliding bearing 13 so that no unnecessary stress is applied between the shaft and the bearings. Thus, a relation between an upper shaft end 17 and the upper bearing 9 is desired to be of pin-point contacting or pivot bearing structure in which little abrasion or heat is produced. However, when the driving magnet and the driven magnet are magnetically coupled with each other in the direction of the radius, there sometimes occurs a deflection and the impeller becomes unstable in the radial direction of the shaft. Thus, a lower shaft end 18 is structured to be in cylindrical contacting relationship with the sliding bearing 13. As a result, the lower bearing provides a fail-safe function.

Figure 4:
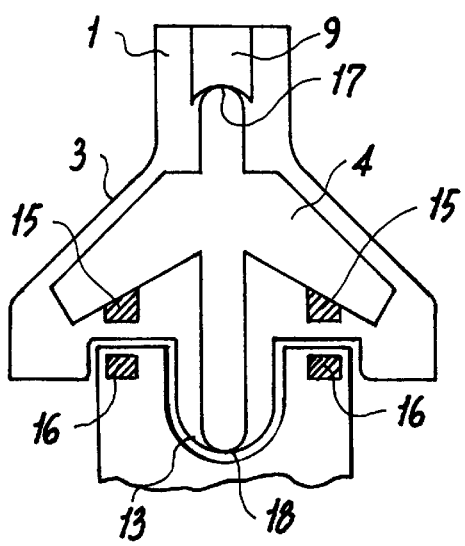
FIG. 4 is a side elevational view in cross-section of another turbo blood pump constructed in accordance with a preferred embodiment of the subject invention with magnetic coupling in the axial direction.

Further, as shown in FIG. 4, it is permissible to place the driven magnet 15 directly on the impeller vane and magnetically couple the driven magnet 15 with the driving magnet 16 located out of the casing 3, in the vertical direction relative to the impeller shaft. When they are magnetically coupled with each other in the vertical direction, the lower shaft end 18 is never deflected in the radial direction of the shaft. Thus, like the relation between the upper shaft end 17 and the upper bearing 9, it is permissible to couple the lower shaft end 18 and the lower bearing 13 with each other in a pin-point contacting or pivot bearing structure.

c. Magnet Material

It is desirable that the driven magnet 15 and driving magnet 16 are formed of material which reduces inertia mass of the impeller and raises pump speed response, so as to increase the stability of impeller rotation and durability of the shaft, and further reduce shearing stresses in the fluid in the pump, thereby reducing hemolysis, and reducing the size of the pump. To satisfy the above requirements, it is preferable that the magnet be a rare earth magnet, for example, neodymium, samarium cobalt or the like.

4. Casing and Other Blood Pump Components

In the blood pump of the present invention, the space (called volute) formed between the impeller vanes and the interior region of the casing should be maintained as small as possible. Although the efficiency of the pump is increased as the space is reduced, too small a space tends to cause blood damage due to the shearing forces produced there between. The desirable clearance has been found to be between 0.1–1.0 mm. Blood flow is also optimized when the casing is formed such that its cross-sectional area is gradually expanded in the flow direction toward the blood exit.

Also, because joints between the casing and the bearings can have microscopic gaps, thrombus formation and hemolysis can easily occur. For this reason, it is desirable that the bearings described above are formed integrally with the casing.

5. Impeller Production Method
a. Synthetic Resin Produced Impeller

If the material of the vane is synthetic resin such as acrylic, polyacrylic, polymetacrylilate, polycarbonate, fluoresin or the like, the impeller can be produced by any of the appropriate methods described below. For example, it is permissible to mold a predetermined shape vane by injection molding polycarbonate and then bond the magnet casing to this vane by adhesive. Or it is permissible to form the vanes and the magnet casing integrally.

b. Metallic Impeller

If the material of the vanes are metal such as stainless steel, titanium, titanium alloy or the like, the impeller can be produced by the same methods as described above for synthetic resin type impellers. For example, it is possible to produce the vane, shaft and magnet casing independently or integrally by lost-wax molding. In lost-wax molding, a male die is made of wax which is replaced by metal or the like. Further, the vane, shaft and magnet casing can be integrally produced. Or the impeller can be produced by cutting stainless steel, titanium, titanium alloy or the like integrally. While the former is suitable for mass production, the latter is suitable for small quantity production of multiple product types.

6. Preferred Embodiment

A preferred embodiment of the turbo blood pump according to the present invention will be described hereinbelow.

FIG. 1 schematically shows a construction of the present invention. The casing 3 comprises an inlet 1 at its upper end and an outlet 2 at the bottom thereof. In a plurality of the vanes of the impeller, driven magnets 15 in the magnet casing 14 at the lower portion are magnetically coupled with the driving magnet 16 located out of the casing 3. Driving magnet 16 is rotated by a motor placed out of the pump. As a result, the impellers and associated driven magnets 15 are rotated so as to supply energy to the blood. The impeller is supported by the shaft 12 and the shaft 12 is supported by the upper bearing 9 and the lower bearing 13. The upper bearing 9 is supported by an upper bearing holder 10.

With continuing reference to FIG. 1, a top face of the vane connecting the upper end 5 of the vane at the entrance and the upper end 7 of the vane at the exit has an angle $\phi$ of 45° with respect to the axis of the shaft 12. A bottom face of the vane connecting the lower end 6 of the vane at the entrance and the lower end 8 of the vane at the exit has an angle $\delta$ of 30° with respect to the axis of the shaft 12. Consequently, fluid flow within the impeller becomes an oblique flow which is neither perpendicular nor parallel to the shaft 12.

Figure 2:
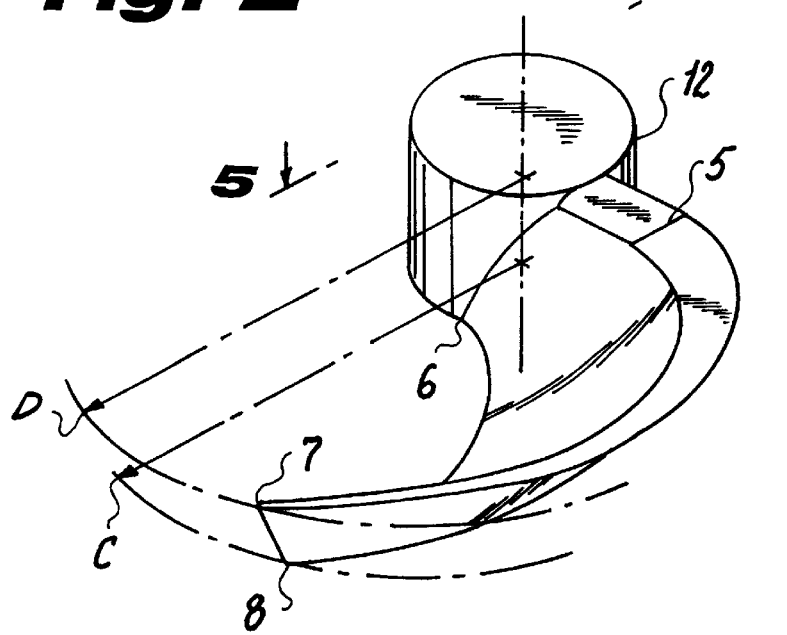
FIG. 2 is a perspective view of a rotary shaft and a vane of an impeller, the vane having a three-dimensional structure formed by twisted curved faces.

Referring now to FIGS. 2 and 5, the upper end 7 and the lower end 8 have different diameters at the distal end of the impeller vane. In addition, the impeller vane has been shaped so as to optimize the flow. More specifically, the vane top face angle $\alpha$—the angle of the upper end of the vane at the exit, relative to circumference D—is designed so as to be smaller than the vane base angle $\beta$—the angle of the lower end of the vane at the exit, relative to circumference C. According to the instant embodiment, the top face angle $\alpha$ is 11° and the base angle $\beta$ is 13°. In the turbo blood pump of the present invention, the impeller vanes are of a three-dimensional structure formed of twisted curved faces, in order to ensure flow efficiency and reduce blood injury. That is, in the instant embodiment, the vane structure 5 described previously is employed. FIG. 2 shows a perspective view of an impeller vane having the three-dimensional structure formed of twisted curved faces.

Referring to FIG. 1, the driven magnet 15 mounted on the impeller vane 4 and the driving magnet 16 mounted outside the casing 3 are magnetically coupled with each other radially relative to the rotary shaft 12. This coupling force produces no axial forces so that the rotary shaft and the bearing are not loaded, thereby improving the durability of the rotary shaft and the bearing. The upper bearing 9 is made of high density polyethylene which is a highly durable synthetic resin.

According to the instant embodiment, a fine ceramic ball 11 is embedded in the upper end of the shaft and made to contact the bearing 9 in pin-point contacting relationship, thereby improving the durability. The entire impeller is formed of stainless steel. The lower bearing 13 is formed in a cylindrical shape and made of a high durability synthetic resin such as high density polyethylene. The impeller shaft 12 is formed in a cylindrical shape corresponding to the shape of the bearing 13. The impeller shaft 12 is supported in face contacting relationship with the lower bearing 13. Because of the face contacting relationship, even if the upper bearing 9 becomes slightly abraded, the lower shaft end 18 will not slip out of the lower bearing 13. This ensures a fail-safe function, thereby contributing to the long-term stability of the rotary shaft.

According to the instant embodiment, both the driving magnet 16 and the driven magnet 15 are made of neodymium. If an electric magnet is installed instead of the driving magnet 16, the driven magnet 15 is rotated by that electric magnet, and an independent motor is not required. Thus, a smaller size, more durable pump is realized.

EXAMPLES

All of the examples provided below are intended to be illustrative of several aspects of the invention. They are not intended to limit the scope or the underlying principles of the invention in any way.

Example 1

A volute type mixed flow pump was used. The height thereof, including the casing, is 38 mm and the diameter thereof is 48 mm. The impeller is of the full-open type to improve antithrombogenicity, having its maximum diameter of 20 mm, and is driven by magnetic coupling having no axial seal. This blood pump shows a discharge rate of 5 l/min at a pressure head of 100 mm Hg under 5,800 rpm, thereby sufficient for replacing the entire cardiac function. The maximum efficient point of the pump is 6.9 l/min in flow rate, 136 mm Hg at the pressure head, and 7,000 rpm in rotation number, so that its maximum total hydraulic efficiency is 66% and specific velocity calculated from the maximum efficient point is 368.

Example 2

Hemolysis Test

With hepalinized fresh bovine blood being used at a blood priming volume of 400 ml, a hemolysis test was conducted under a condition in which the flow rate was 5 l/min, at a pressure head of 100 mm Hg for 0–5 hours. The same test was conducted by means of a commercially available Delphin pump. Table 1 shows the results, according to which the hemolytic index is 0.015 g/100 l, which is less than half the hemolytic index of 0.033 g of the Delphin pump.

TABLE 1

(Result of Hemolysis test)

| Blood | | | Fresh bovine blood | |
|---|---|---|---|---|
| Priming volume (ml) | | | 400 | |
| Flow rate(ml/min) | | | 5,000 | |
| Pressure head (mmHg) | | | 100 | |
| Pump | A mixed flow pump | | Delphin pump | |
| Time (min) | Ht | Free Hb | Ht | Free Hb |
| 0 | 32.4 | 10 | 32.1 | 8 |
| 30 | 31.5 | 20 | 31.5 | 24 |
| 60 | 31.9 | 27 | 31.9 | 41 |
| 120 | 32.8 | 51 | 30.9 | 76 |
| 180 | 33.7 | 62 | 31.6 | 118 |
| 240 | 32.4 | 79 | 31.9 | 155 |

HI= (100 − Ht)CV/100 QT  Q: Blood Flow rate (ml/min)
HI: Hemolysis index  T: Time (min)
Ht: Hematocrit (%)
C: Increase of free hemoglobin (mg/dl)
V: Priming volume (ml)

What is claimed is:

1. A turbo blood pump comprising:
   a) a casing having an interior region, an aperture formed in an upper portion of said casing defining a blood inlet, and an aperture formed in a lower portion of said casing defining a blood outlet;
   b) an impeller rotatably mounted about a vertical axis within said interior region, said impeller including:
      1) a rotary shaft, and
      2) at least one vane depending from said rotary shaft, said at least one vane having an upper radius adjacent said blood inlet and a lower radius adjacent said blood outlet, said upper radius being less than said lower radius, and the base of said at least one vane forming an exterior angle of less than 65° with the axis of said rotary shaft; and
   c) a driving means for rotating said impeller about the vertical axis.

2. The turbo blood pump according to claim 1, wherein a partial face of said at least one vane includes a three-dimensional structure which is not in parallel to the rotary axis of said impeller.

3. The turbo blood pump according to claim 1, wherein said at least one vane includes a three-dimensional structure formed of twisted curved faces.

4. The turbo blood pump according claim 1, wherein the distal portion of said at least one vane includes a vane top face angle and a vane base angle and said top face angle is unequal to said vane base angle.

5. The turbo blood pump according to claim 1, wherein the distal portion of said at least one vane includes a vane top face angle and a vane base angle and said top face angle is smaller than said vane base angle.

6. The turbo blood pump according to claim 1, wherein the upper portion of said impeller rotary shaft is rotatably supported in a pivot bearing structure and the lower portion of said impeller rotary shaft is rotatably supported in a sliding bearing structure, said sliding bearing of a cylindrical face contacting type, and
   wherein said driving means for rotating said impeller includes a driven magnet mounted on said at least one vane and a driving magnet mounted radially adjacent said driven magnet and outside said casing, whereby said driven magnet is magnetically coupled with said driving magnet.

7. The turbo blood pump according to claim 1, wherein said impeller includes at least one vane-attaching disk connecting adjacent vanes depending from said rotary shaft.

8. The turbo blood pump according to claim 1, wherein said interior region of said casing increases in diameter from said blood inlet to said blood outlet.

9. A turbo blood pump comprising:
   a) a casing having an interior region, an aperture formed in an upper portion of said casing defining a blood inlet, and an aperture formed in a lower portion of said casing defining a blood outlet;
   b) an impeller rotatably mounted about a vertical axis within said interior region, said impeller including:
      1) a rotary shaft, and
      2) at least one vane depending from said rotary shaft, said at least one vane having an upper radius adjacent said blood inlet and a lower radius adjacent said blood outlet, said upper radius being less than said lower radius, and a partial face of said at least one vane including a three dimensional structure which is not parallel to the rotary axis; and
   c) a driving means for rotating said impeller about the vertical axis.

10. The turbo blood pump according to claim 9, wherein the base of said at least one vane forms an exterior angle of less than 90° with the axis of said rotary shaft.

11. The turbo blood pump according to claim 9, wherein the distal portion of said at least one vane includes a vane top face angle and a vane base angle and said top face angle is unequal to said vane base angle.

12. The turbo blood pump according to claim 9, wherein the distal portion of said at least one vane includes a vane top face angle and a vane base angle and said top face angle is smaller than said vane base angle.

13. The turbo blood pump according to claim 9, wherein the upper portion of said impeller rotary shaft is rotatably supported in a pivot bearing structure and the lower portion of said impeller rotary shaft is rotatably supported in a sliding bearing structure, said sliding bearing of a cylindrical face contacting type; and
   wherein said driving means for rotating said impeller includes a driven magnet mounted on said at least one vane and a driving magnet mounted radially adjacent said driven magnet and outside said casing, whereby said driven magnet is magnetically coupled with said driving magnet.

14. The turbo blood pump according to claim 9, wherein said impeller includes at least one vane-attaching disk connecting adjacent vanes depending from said rotary shaft.

15. The turbo blood pump according to claim 9, wherein said interior region of said casing increases in diameter from said blood inlet to said blood outlet.

16. A turbo blood pump comprising:
   a) a casing having an interior region, an aperture formed in an upper portion of said casing defining a blood inlet, and an aperture formed in a lower portion of said casing defining a blood outlet;

b) an impeller rotatably mounted about a vertical axis within said interior region, said impeller including:
1) a rotary shaft, and
2) at least one vane depending from said rotary shaft, said at least one vane having an upper radius adjacent said blood inlet and a lower radius adjacent said blood outlet, said upper radius being less than said lower radius, and said at least one vane including a three-dimensional structure formed of twisted curved faces; and c) a driving means for rotating said impeller about the vertical axis.

17. The turbo blood pump according to claim 16, wherein the base of said at least one vane forms an exterior angle of less than 90° with the axis of said rotary shaft.

18. The turbo blood pump according to claim 16, wherein the distal portion of said at least one vane includes a vane top face angle and a vane base angle and said top face angle is unequal to said vane base angle.

19. The turbo blood pump according to claim 16, wherein the distal portion of said at least one vane includes a vane top face angle and a vane base angle and said top face angle is smaller than said vane base angle.

20. The turbo blood pump according to claim 16, wherein the upper portion of said impeller rotary shaft is rotatably supported in a pivot bearing structure and the lower portion of said impeller rotary shaft is rotatably supported in a sliding bearing structure, said sliding bearing of a cylindrical face contacting type, and wherein said driving means for rotating said impeller includes a driven magnet mounted on said at least one vane and a driving magnet mounted radially adjacent said driven magnet and outside said casing, whereby said driven magnet is magnetically coupled with said driving magnet.

21. The turbo blood pump according to claim 16, wherein said impeller includes at least one vane-attaching disk connecting adjacent vanes depending from said rotary shaft.

22. The turbo blood pump according to claim 16, wherein said interior region of said casing increases in diameter from the blood inlet to the blood outlet.

23. A turbo blood pump comprising:
a) a casing having an interior region, an aperture formed in an upper portion of said casing defining a blood inlet, and an aperture formed in a lower portion of said casing defining a blood outlet;
b) an impeller rotatably mounted about a vertical axis within said interior region, said impeller including:
1) a rotary shaft, and
2) at least one vane depending from said rotary shaft, said at least one vane having an upper radius adjacent said blood inlet and a lower radius adjacent said blood outlet, said upper radius being less than said lower radius, the distal portion of said at least one vane including a vane top face angle and a vane base angle, said top face angle is unequal to said vane base angle; and
c) a driving means for rotating said impeller about the vertical axis.

24. The turbo blood pump according to claim 23, wherein said vane top face angle is smaller than said vane base angle.

25. The turbo blood pump according to claim 23, wherein the base of said at least one vane forms an exterior angle of less than 90° with the axis of said rotary shaft.

26. The turbo blood pump according to claim 25, wherein said at least one vane includes a three-dimensional structure formed of twisted curved faces.

27. The turbo blood pump according to claim 23, wherein the upper portion of said impeller rotary shaft is rotatably supported in a pivot bearing structure and the lower portion of said impeller rotary shaft is rotatably supported in a sliding bearing structure, said sliding bearing of a cylindrical face contacting type, and wherein said driving means for rotating said impeller includes a driven magnet mounted on said at least one vane and a driving magnet mounted radially adjacent said driven magnet and outside said casing, whereby said driven magnet is magnetically coupled with said driving magnet.

28. The turbo blood pump according to claim 23, wherein said impeller includes at least one vane-attaching disk connecting adjacent vanes depending from said rotary shaft.

29. The turbo blood pump according to claim 23, wherein said interior region of said casing increases in diameter from the blood inlet to the blood outlet.

30. A turbo blood pump comprising:
a) a casing having an interior region, an aperture formed in an upper portion of said casing defining a blood inlet, and an aperture formed in a lower portion of said casing defining a blood outlet;
b) an impeller rotatably mounted about a vertical axis within said interior region, said impeller including:
1) a rotary shaft, and
2) at least one vane depending from said rotary shaft, said at least one vane including a driven magnet attached thereto;
c) a pivot bearing structure mounted in said casing and rotatably supporting the upper portion of said impeller rotary shaft;
d) a sliding bearing structure mounted in said casing and rotatably supporting the lower portion of said impeller rotary shaft, said sliding bearing of a cylindrical face contacting type; and
e) a driving magnet mounted radially adjacent said driven magnet and outside said casing, whereby said driven magnet is magnetically coupled with said driving magnet and rotates said impeller about the vertical axis.

31. The turbo blood pump according to claim 30, wherein the base of said at least one vane forms an exterior angle of less than 90° with the axis of said rotary shaft.

32. The turbo blood pump according to claim 31, wherein said at least one vane includes a three-dimensional structure formed of twisted curved faces.

33. The turbo blood pump according to claim 30, wherein the distal portion of said at least one vane includes a vane top face angle and a vane base angle and said top face angle is unequal to said vane base angle.

34. The turbo blood pump according to claim 30, wherein the distal portion of said at least one vane includes a vane top face angle and a vane base angle and said top face angle is smaller than said vane base angle.

35. The turbo blood pump according to claim 34, wherein said impeller includes at least one vane-attaching disk connecting adjacent vanes depending from said rotary shaft.

36. The turbo blood pump according to claim 34, wherein said interior region of said casing increases in diameter from the blood inlet to the blood outlet.

* * * * *